(12) United States Patent
Gaugler

(10) Patent No.: US 6,474,259 B1
(45) Date of Patent: Nov. 5, 2002

(54) APPARATUS AND METHOD FOR MASS PRODUCTION OF INSECTICIDAL NEMATODES

(75) Inventor: Randy Gaugler, New Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 09/845,816

(22) Filed: Apr. 30, 2001

(51) Int. Cl.[7] .............................................. A61K 29/00
(52) U.S. Cl. ....................................................... 119/6.7
(58) Field of Search ........................... 119/6.7, 6.8, 455, 119/458

(56) References Cited

U.S. PATENT DOCUMENTS

| 3,148,649 | A | * | 9/1964 | Moore et al. | 119/6.8 |
|---|---|---|---|---|---|
| 3,927,642 | A | * | 12/1975 | Levin | 119/6.8 |
| 5,023,183 | A | * | 6/1991 | Friedman et al. | 119/6.7 |
| 5,466,448 | A | * | 11/1995 | Smart, Jr. et al. | 119/6.7 |
| 5,694,883 | A | * | 12/1997 | Tachibana | 119/6.7 |
| 5,932,237 | A | * | 8/1999 | Raulston et al. | 119/6.7 |
| 6,223,687 | B1 | * | 5/2001 | Windle | 119/6.7 |

* cited by examiner

Primary Examiner—Charles T. Jordan
Assistant Examiner—Elizabeth Shaw
(74) Attorney, Agent, or Firm—Licata & Tyrrell P.C.

(57) ABSTRACT

Disclosed are an apparatus and methods for in vivo mass production of insecticidal nematodes, which the efficiency and volume of nematode production. In the method, nematodes are cultured within a natural insect host. The apparatus comprises at least one harvesting area, a water dispensing system that promotes harvest of nematodes from the host organisms, and a water collection and concentration system for nematode collection and storage. The harvesting area comprises reusable stackable perforated trays, which allow passage of dispensed water while retaining the nematode hosts. The perforations are sized to retain the host organisms and facilitate the passage of harvested nematodes carried within the dispensed water.

25 Claims, 6 Drawing Sheets

APPARATUS AND METHOD FOR MASS PRODUCTION OF INSECTICIDAL NEMATODES

FIELD OF THE INVENTION

This invention relates to the field of agriculture and biological control of insect pests. In particular, the invention provides an apparatus and methods for low-cost mass production of insecticidal nematodes.

BACKGROUND OF THE INVENTION

Heightened awareness of the dangers of chemical insecticides, combined with passage of the Federal Food Quality Protection Act restricting usage of these insecticides, has further increased the need for alternative insect control measures. Use of biological insecticides, in particular entomopathogenic nematodes, are consequently becoming an increasingly viable alternative to control insect pest populations.

Nematodes are simple, colorless, unsegmented roundworms that lack appendages. They may be free-living, predaceous or parasitic. The entomopathogenic nematodes of the genera Steinernema and Heterorhabditits are insect parasitic nematodes that possess an optimal balance of attributes to enable their use as biological control agents for insect pests.

Steinernema and Heterorhabditis have similar life cycles. The non-feeding infective juvenile seeks out insect hosts and penetrate into the insect body. There the juvenile releases a symbiotic bacterium, (Xeneorhabdus for steinernematids, Photorhadbdus for heterorhabditids), which multiplies rapidly and causes insect death. The nematodes feed upon the bacteria and liquefying insect, and mature into adults. The life cycle is completed in a few days, and hundreds of thousands of new infective juveniles emerge from the insect cadaver in search of fresh insect hosts.

Numerous benefits are derived by the use of nematodes as opposed to chemical insecticides or other biological methods. For example, nematodes are lethal to a greater number of important soil insect pests but are completely safe for plants and animals. Further, most chemical insecticides and biologicals require days or even weeks to kill insect pests, whereas nematodes usually kill most insect pests within 24–48 hours.

The two genera of entomopathogenic nematodes comprise nearly 30 species that are useful as biological control agents against a large number of insect pests, including artichoke plume moth, root weevils, cranberry girdler, sciarids, wood borers, fungus gnats, scarabs, mole crickets billbugs, armyworm, cutworm and webworm.

Unfortunately, for nematodes to represent a commercially viable alternative to chemical insecticides a self-contained, low cost system of production is preferable if not necessary. However, current methods of nematode production present tedious multi-step procedures involving sterilization techniques and expensive equipment, resulting in high production costs and contamination problems.

Moreover, though some of the above-described systems have been used on a small scale, a major difficulty arises when scale-up of nematode production is attempted. In vivo systems have proven difficult to scale-up. Temperature and humidity are the only wholly controllable process parameters. Spraying insect hosts with infective juveniles can accelerate the inoculation step, or the insects can be dipped into a nematode suspension. But harvesting emerging infective juveniles has remained an intractable bottleneck. In the laboratory, the White trap has been the traditional method of collecting entomopathogenic nematodes. In the White trap, infected insect cadavers are placed within a topless petri plate and the plate is placed in a tray of water. As the nematodes complete their development and emerge to seek new insect hosts, they exit the cadaver into the tray of water and are unable to escape. Nematodes are thus collected in the tray water. Scale-up of harvesting has consisted of simply providing larger White traps, usually by placing several dishes within a large tray. Because nematode lateral migration from the host cadaver to the water reservoir is required, increasing dish diameter beyond 150 mm quickly becomes counterproductive.

Carne and Reed (1964) described a harvest apparatus in which cadavers would be supported on nematode-permeable disks resting in the mouth of a series of large funnels. Water level in the funnels would be maintained at cadaver height by a common constant-level device. Emerging infective juveniles would pass through the disk and settle to the funnel bottom where they would be collected by opening the stopcock. The key innovation of the system was the use of perforated plates, which nematodes could migrate through to the water reservoir, reducing the need for significant lateral migration. There are no reports that the design was tested, and its design does not lend itself to successful scale-up, inasmuch as the funnel system would be prone to clogging before a significant number of nematodes could be collected.

Other methods for nematode production involve sterilized culture vessels, expensive and time consuming development and sterilization of media for nematode growth, and the introduction of nematodes into a bacterial suspension into the sterile environment. Accordingly, an urgent need exists for improved apparatus and methods for mass production, harvest and storage of insecticidal nematodes.

SUMMARY OF THE INVENTION

The present invention features an apparatus and method for in vivo production of parasitic nematodes. In accordance with the method of the invention, nematodes are cultured within a natural insect host. The apparatus comprises at least one harvesting area, a water dispensing system that promotes harvest of nematodes from the host organisms, and a water collection and concentration system for nematode collection and storage. In a preferred embodiment, the harvesting area comprises reusable stackable perforated trays preferably constructed from a non-toxic material such as plastic or aluminum. The perforated material allows passage of dispensed water from the water dispensing system while retaining the nematode hosts. The perforations are sized to retain the host organisms and facilitate the passage of harvested nematodes carried within the dispensed water.

Inoculation of the host organism is achieved by a simple dip or spray process where the host organisms are supported by a perforated tray and dipped or sprayed with a nematode suspension. During the initial phase of nematode infection, the nematodes release bacteria that are symbiotes of the nematodes, but that kill the host organism within 24 to 48 hours. The nematodes then reproduce within the host organism. During this phase, while the nematodes feed off the bacteria decomposing host tissue, the incubation chamber is maintained at a temperature and humidity suitable for maximum nematode growth and utilization of bacterial and host insect cadaver food sources. Within a determinable number of days of the initial inoculation, the host organism bursts open, releasing adult nematodes. At this time, the incubation area is sprayed or otherwise contacted with water or another aqueous medium, washing the nematodes away from the host organisms and allowing their collection and concentration in bulk form.

The water dispenser system includes at least one nozzle that is positioned at an angle effective for the removal of the incubated nematodes from the infected host organisms. Water is released from the nozzle as a fine mist or spray ensuring removal of the nematodes from the host organism and not removal of the host organism itself. The perforated trays allow passage of water through the system thereby flushing the nematodes towards a collection area. Effluent generated by the water dispensing system and carrying the nematodes passes through the supporting trays towards a collection area consisting of a flat solid surface with side walls angularly placed to direct the flow of liquid toward a nematode concentration system and storage vessel.

Other features and advantages of the present invention will be understood by reference to the drawings and detailed description that follow.

DETAILED DESCRIPTION OF THE INVENTION

Figure 1:
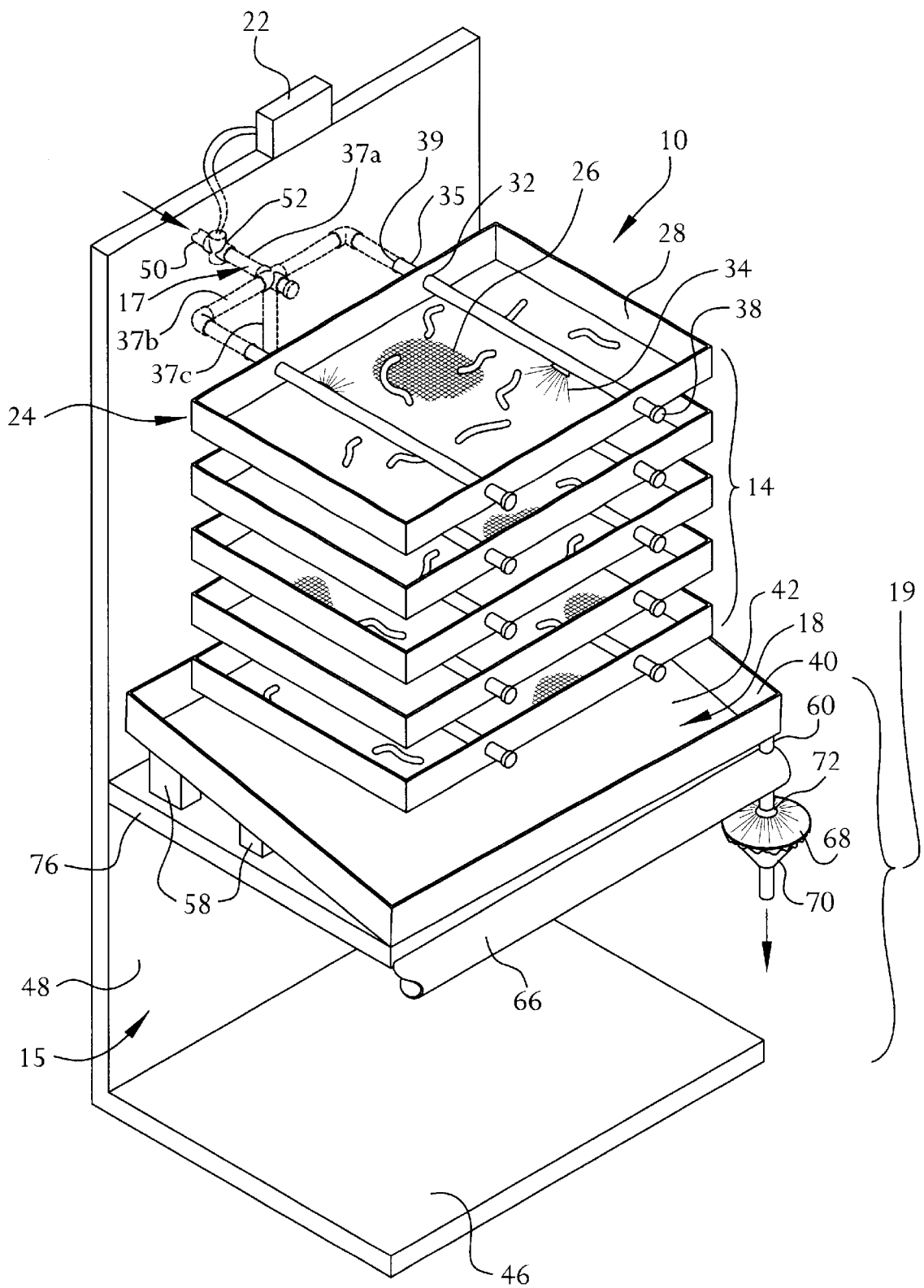
FIG. 1 is an isometric view of a preferred embodiment of a nematode production apparatus according to the present invention.
Figure 2:
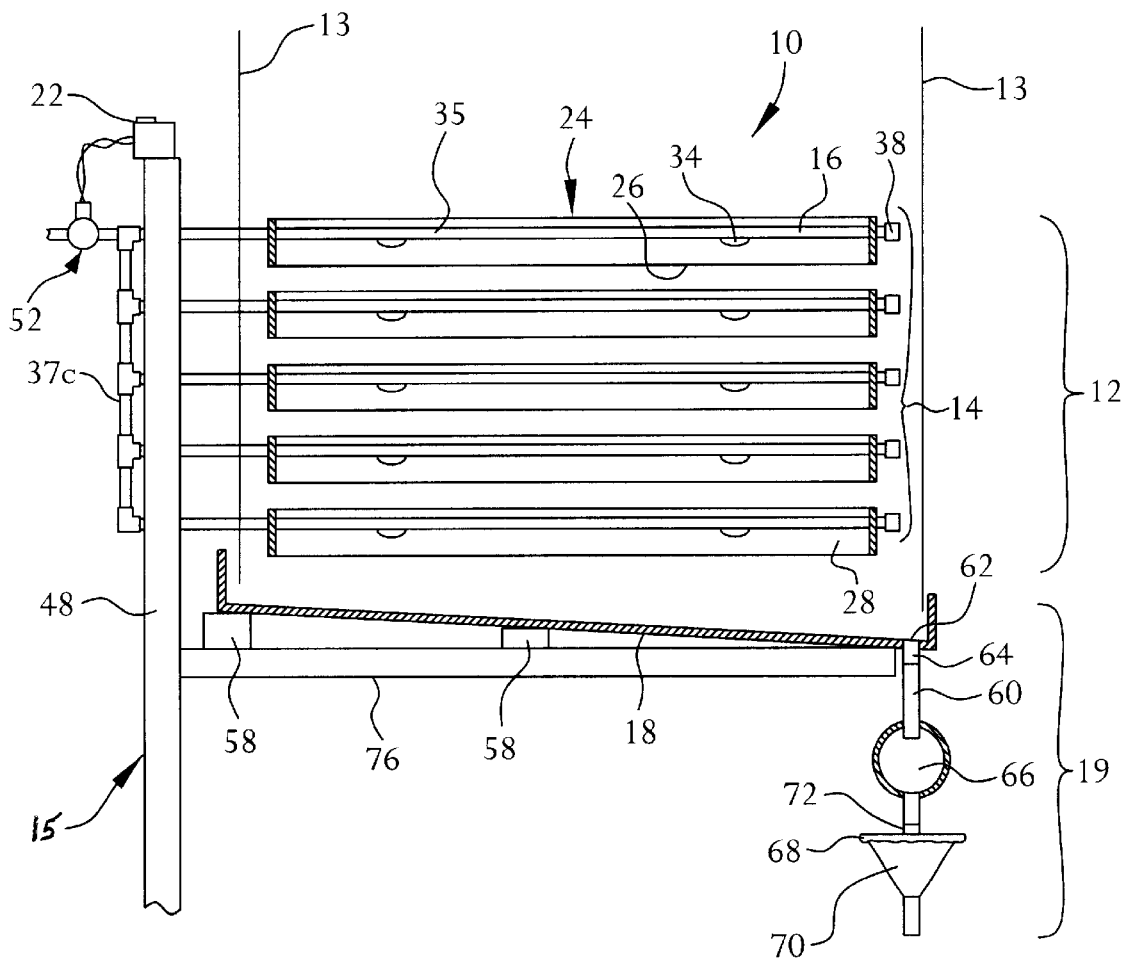
FIG. 2 is a side view of the apparatus illustrated in FIG. 1.
Figure 3:
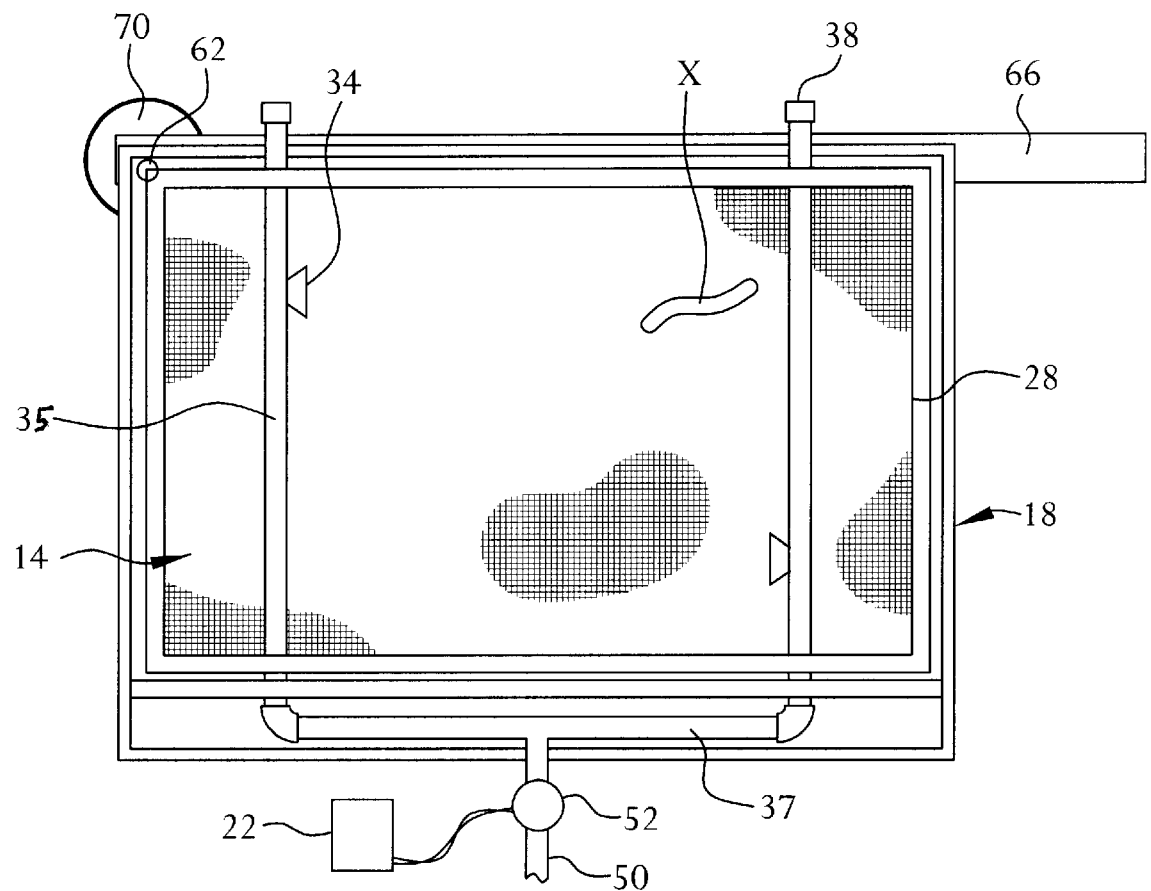
FIG. 3 is a top view of the apparatus illustrated in FIG. 1.
Figure 4:
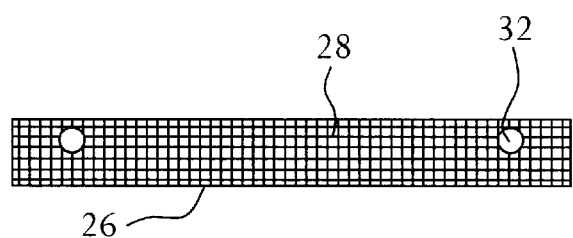
FIG. 4 is a side view of a tray illustrated in FIGS. 1–3.

The present invention provides an apparatus and method for low-cost, high-efficiency mass production of insecticidal nematodes. The method makes use of the natural lifecycle of entomopathogenic nematodes, wherein juveniles infect and kill host insects, multiply and grow to adulthood inside insect cadavers, then produce new infective juveniles that burst from the cadavers and exit into the surrounding medium. A basic apparatus of the invention features a harvesting area that supports one or more flat trays or similar surfaces comprised of a perforated material that retains the host organism thereon, but that allows passage of nematodes through it. Nematode-inoculated host organisms are incubated (in the apparatus or in a separate incubation area) at a desired temperature and humidity for a determinable period of time, until the host cadavers are expended as a food source. Emergence of the adult nematodes is facilitated in the harvesting area by spraying, flushing, or otherwise contacting the cadavers with water, to trigger the emergence of the nematodes and to wash the nematodes away from the cadavers and through the perforated surface of the holding trays, to a collection and concentration system. Thus, in addition to the support system for the holding trays, the apparatus features a water dispensing system for facilitating emergence and separation of the nematodes, as well as a collection and concentration system.

The apparatus and method of the present invention are suitable for mass production of any entomopathogenic nematode, including any one of the more than 30 species of Steinernema and Heterorhabditis. Moreover, any insect host of a selected nematode species may be utilized in the method, and the timing of incubation and nematode harvest calculated based on the lifecycle of the nematode in a particular host, as would be known in the art. A preferred insect host for use in the invention is the greater wax moth, *Galleria melonella*. Another preferred host is the mealworm, *Tenebrio molitor*. Other insect hosts suitable for use in the invention include, but are not limited to, artichoke plume moths, root weevils, cranberry girdlers, sciarids, wood borers, fungus gnats, scarabs, mole crickets billbugs, armyworms, cutworms and webworms.

The method of the invention comprises four basic steps: (1) inoculation of host organisms with infective juvenile nematodes; (2) incubation of the infected hosts; (3) harvesting the expanded population of nematodes from the spent host cadavers; and (4) collecting the harvested nematodes. In a preferred embodiment of the present invention, all four basic steps are accomplished through the use of an integrated apparatus comprising inoculation, incubation, harvesting and collection functions. However, an equally viable alternative embodiment comprises separating the inoculation and/or incubation functions from the harvesting/collection functions. These alternative embodiments will be readily understood from the detailed description that follows.

The materials used in the invention for constructing the holding tray, collector, storage vessel(s) and concentration system should inert materials. that are non-toxic to the nematodes. Such materials include, but are not limited to, aluminum, plastics, glass, teflon, and non-metallic substances. In addition, the holding tray must be capable of having a perforated bottom that supports nematode infected host organisms while allowing passage of nematodes.

Supporting structures (e.g., various housings and support beams to hold the apparatus in place) that do not come into contact with the nematodes may comprise any commonly available construction materials. In the preferred embodiment wherein the water conveyance system also is a support rod, it is preferable that these are constructed of PVC pipe or another material non-toxic to nematodes. An advantage to using PVC pipe is that PVC pipe may be easily adjusted to vary the size or shape of the apparatus. For example, PVC pipe may be shortened to accommodate smaller trays or the PVC pipe may be configured to accommodate trays of variable dimensions.

If the apparatus is integrated to comprise an incubation chamber, this may be made of any material commonly used to construct an incubation chamber. For instance, the chamber may simply comprise plastic sheets surrounding the harvesting area. Alternatively, the harvesting area may be placed in an enclosed housing made of plastic or other material that enables maintenance of high humidity.

The holding tray on which the inoculation, incubation and harvesting steps take place, is a central feature of the apparatus of the invention. The tray has a substantially flat bottom piece with perforations and, preferably, raised side portions. In one embodiment of the invention, the tray has a substantially rectangular shape. However, the tray may embody any geometrical configuration. For instance, it may have a circular or elliptical shape with a single wall extending from its periphery. Another embodiment comprises a polygon shaped tray, having a plurality of linear raised side portions extending from their peripheries. The perforated bottom of the holding tray facilitates both passage of water from the water dispensing system and inoculation of the nematode host organisms.

The perforated bottom piece comprises perforations sufficiently large to allow passage of nematodes through the tray bottom, but small enough that the insect hosts are retained in the tray. The raised sides and the bottom of the tray may be made of a single piece of material, folded upward so as to form the sides. Alternatively, the raised sides and the flat bottom may be made separately, then joined at the outer edge of the flat bottom perforated piece.

Preferably, two or more holding trays are stacked for incubation and harvesting. Stacking of trays efficiently uses available horizontal and vertical space, allowing for high nematode production per given area.

The preferred method of inoculating host organisms is to place them on a holding tray and dip them into an aqueous suspension of nematodes. An alternative method is to spray the insects with the nematode suspension. In either method, the perforated bottom of the tray allows the excess nematode inoculation water to flow out of the tray.

Numerous benefits arise from this method of inoculation. The need for additional transfer steps and equipment are eliminated due to the multifunctional tray that serves as an inoculation tray, incubation tray and harvesting tray. It is not necessary to transfer the host organisms to another support system upon inoculation. Once the tray is dipped or sprayed, the nematode infected hosts are placed into an incubation chamber.

As mentioned above, the incubation chamber may be an integral part of the harvesting apparatus. In one embodiment, a harvesting area comprising a single stack of trays is enclosed within an incubation chamber. In another embodiment, several stacks are enclosed within an incubation chamber. In an embodiment adapted for larger-scale production, several harvesting units simply may be placed in a walk-in incubation chamber.

In the method of the invention, the nematode infected hosts are placed within the incubation chamber and incubated at high humidity for 5 to 10 days, or another appropriate period of time pre-determined after selecting the host organism. Preferably, the humidity within the chamber is 100% but the humidity can range from about 50% to 100%, again depending on the host organism.

Following the incubation period, infective juvenile nematodes are induced to emerge from the insect cadavers by contacting the cadavers with free water or a water containing water. Water from any source may be utilized, as long as it does not contain impurities or contaminants that would be harmful to the nematodes.

Figure 5:
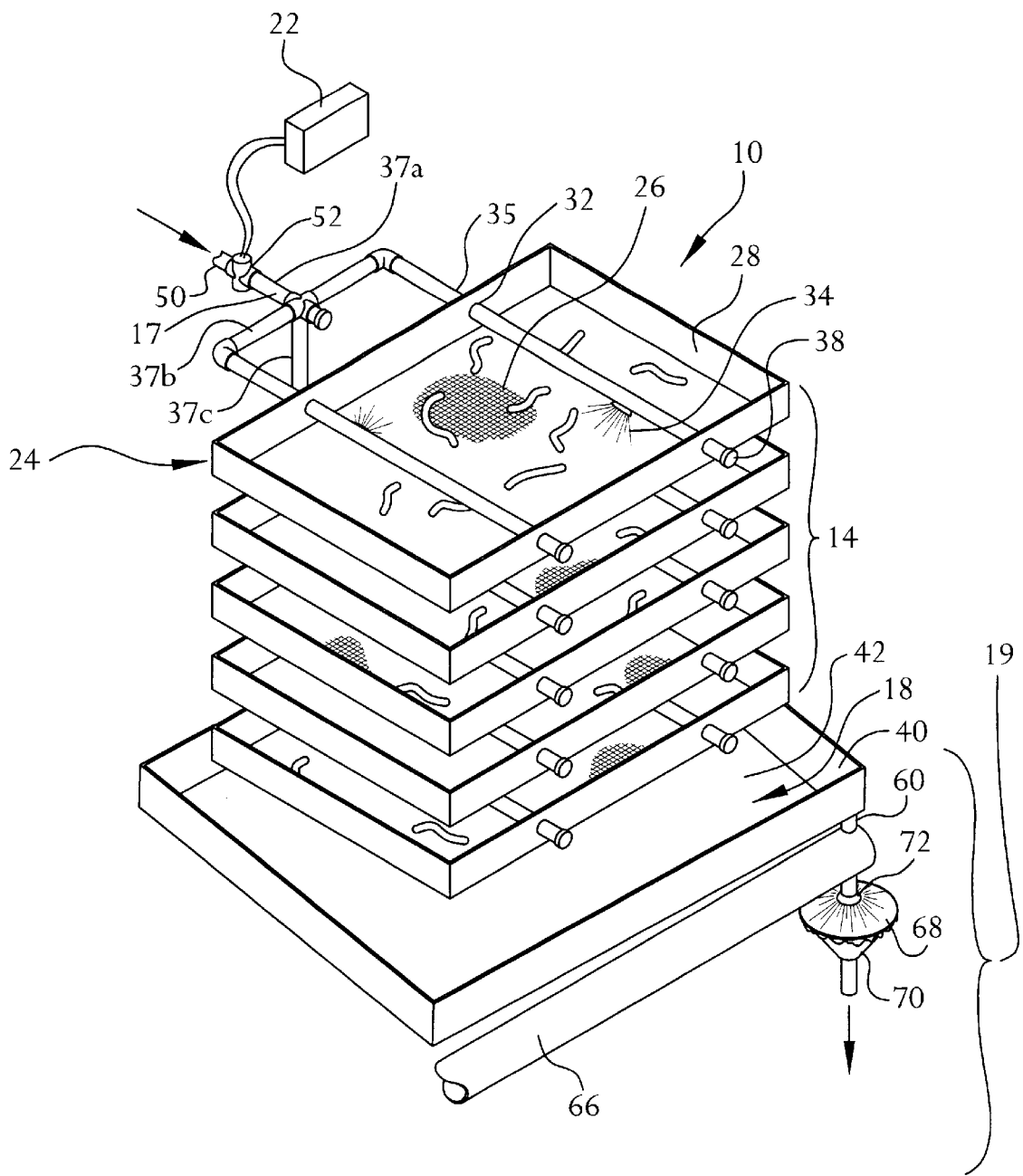
FIG. 5 is an isometric view of another preferred embodiment of the apparatus of the invention.
Figure 6:
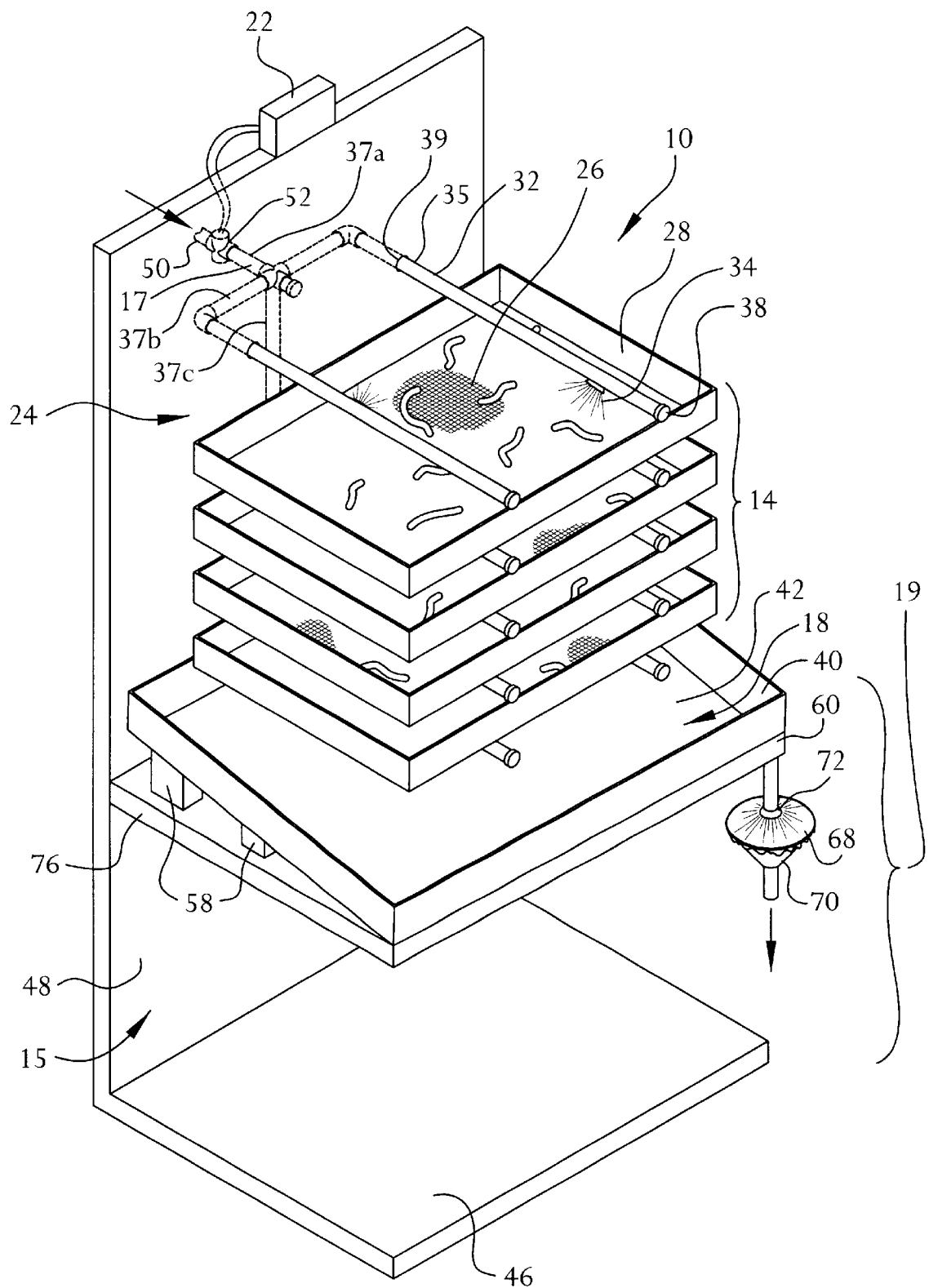
FIG. 6 is an isometric view of another preferred embodiment of the apparatus of the invention.
Figure 7:
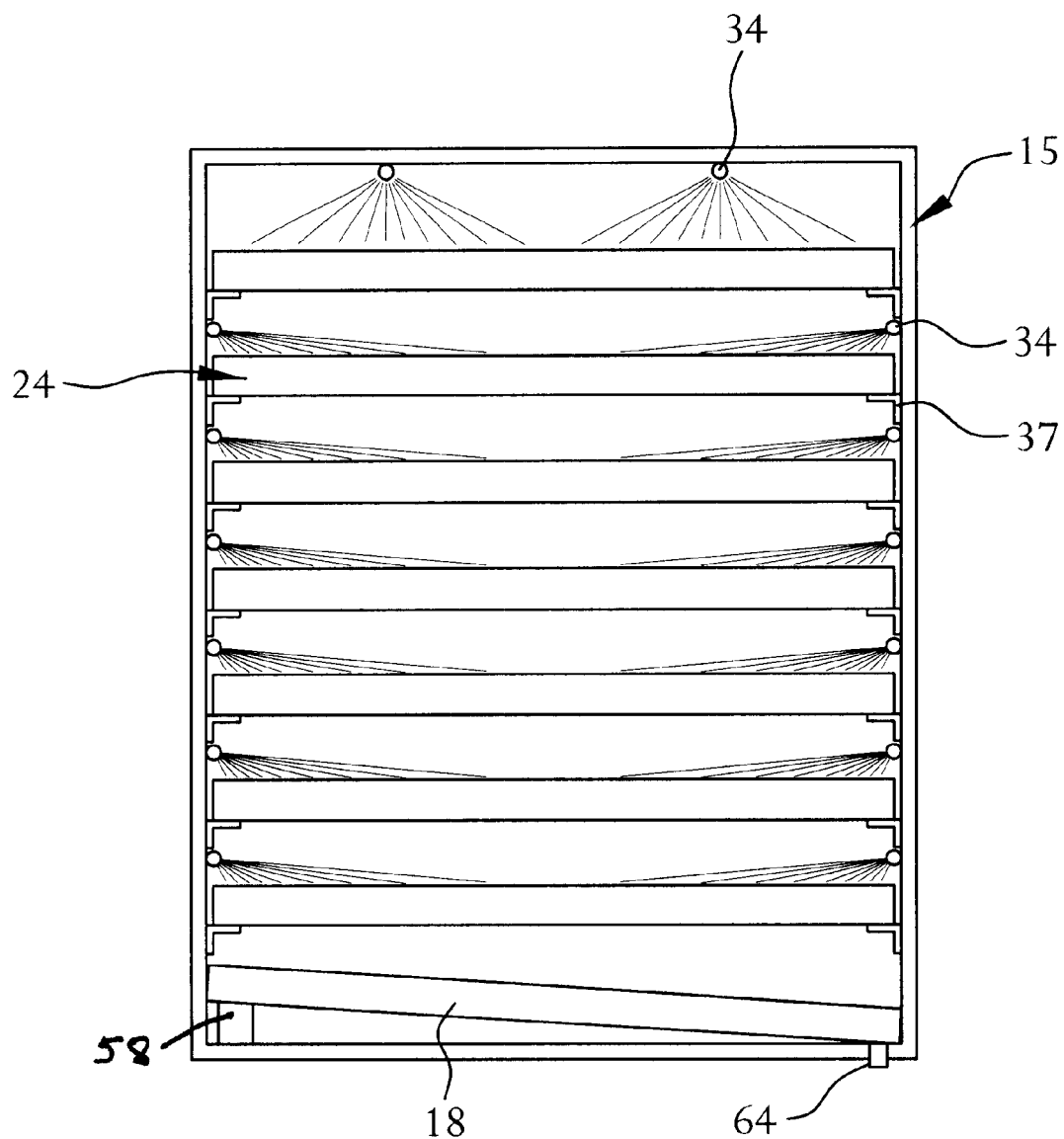
FIG. 7 is a front view of another preferred embodiment of the apparatus of the invention.

In the apparatus of the invention, which is designed specifically for efficient harvesting of the nematodes, it is preferred that the holding trays are arranged one on top of another, with a constant and equidistant spacing between them. Trays are supported on a series of horizontal support rods, which may serve a dual function as a water dispensing system. One example of this embodiment is illustrated in FIGS. 1–5, wherein the holding tray comprises apertures through parallel raised sides, and the trays slide onto the support rods through the apertures. Another example of this embodiment is illustrated in FIG. 6, wherein the holding trays simply rest upon the horizontal support rods, and each level of support rod/water conduit supplies water to the tray that rests below it. In another embodiment, the horizontal support rods may serve simply for support and the water conveyance dispensing system may comprise tubing affixed or mounted to the support rods. In an alternate embodiment, the frame or housing of the apparatus may be constructed with side walls fitted with holding tray support means, such as rails, pegs, ledges, or any similar type of fitting that enables the holding trays to slide in and out of the housing. This embodiment is shown in FIG. 7. Such tray support means are well known in the art, being customarily found on any cabinet or housing in which trays or shelves are removably located. Further, such tray support means can be made adjustable, such that the distance between trays may be increased or decreased as desired.

As mentioned, the water conveyance system in the embodiment shown in FIGS. 1–5 comprises in part the holding tray support arms, serving a dual function. In another embodiment, the water conveyance system comprises tubing affixed to the support rods. In yet another embodiment, the water conveyance system comprises tubing affixed to or contained within side and/or rear walls of the frame or housing. In any of the configurations described above, the water conveyance system comprises dispensing portals or nozzles arranged such that the water is misted or sprayed onto each of the holding trays, in a substantially angled or downward arc, thereby facilitating movement of the emerging nematodes through the perforated bottoms of the trays to the collection system.

Water dispensing preferably is controlled by a timing device. Nematode emergence from host cadavers is induced by contact with the water. Emerging nematodes are washed through the holding trays using a water-dispensing cycle comprising spraying or misting the cadavers for, e.g., 3 minutes at 4-hour intervals for a total duration ranging from 1–5 days, preferably 2–3 days, depending on the nematode and host species. During this cycle, the dispensed water is continually flowing through the perforated bottoms of the holding trans and into a collecting tray that is positioned at an angle to direct the flow of water towards a single drain point. The dispensed water continually collects nematodes that emerge from the nematode infected hosts.

The collection/storage system of the apparatus of the present invention comprises the above-described angled collection tray, which directs the flow of nematodes into a drain tube and ultimately to a storage and/or concentration system. In a simple embodiment, the dispensed water comprising the harvested nematodes flows through the drain tube directly into a wash or storage container, such as a large plastic jug. Preferably, however, the nematode-containing water flows through a filter of appropriate pore size to retain insect cadavers and other debris, and to enable nematodes to pass through. A preferred material for this use is organdy fabric, which is commonly available.

In one embodiment, the filter is placed in a funnel and gravity is used to funnel the water through to the wash and storage tank. In another embodiment, external pressure as a substitute for gravity is applied externally to the filter, thereby pulling the nematode enriched solution through the filter. In the alternative, suction may be applied externally to the filter to aid in directing the flow of nematode enriched water through the collection funnel and to the wash and/or storage tank.

In another preferred embodiment, the harvested nematodes from several units may be collected together into a common storage unit, via a collection pipe to which the drain tube from each unit is attached. This embodiment lends itself to the inclusion of a concentration system as well. A preferred method of concentrating the nematodes involves flow-through cross-filtration. In this embodiment, the collection pipe consists of an inner tube within the collection pipe, wherein the inner tube comprises a penetrable membrane, such as an osmotic membrane, allowing transport of material smaller than the membrane cutoff, the size of which is selected such that the inner tube retains the nematodes while allowing the passage of water across the membrane and thus concentrating the nematode solution within the inner tube. The outer tube that surrounds the inner tube retains the water removed from the nematode enriched water, which may be discarded. The concentrated nematode filtrate is then collected in a collection vessel comprised of a plastic material or aluminum.

Other methods of concentrating the harvested nematodes will be apparent to persons of skill in the art. For instance, a second simple funnel and filter system may be utilized, employing a filter with size cutoff to retain the nematodes. This system may operate by gravity or by positive or negative pressure, as described for the initial filter.

Another advantage of the present invention is the ease with which the apparatus may be cleaned. The trays are removable and are cleaned separately. In addition, a cleaning agent and/or disinfectant can be passed through the water dispensing system and allowed to flow through the system removing possible contaminants. Therefore, the water dispensing system provides for both the harvesting of the nematodes as well as passage of the cleaning solution.

Referring now to the drawings, wherein like numerals indicate like elements, there is shown in FIG. 1 an illustration of one embodiment of an apparatus designated generally 10 for mass production of insecticidal nematodes. In FIG 1, an apparatus 10 includes a harvesting area 14, a support system 15, a water dispensing system 17, and a collection system 19. If the apparatus is integrated for incubation and harvesting as shown in FIG. 2, the incubation chamber 12 is fully or partially enclosed by an enclosure material 13 that enables maintenance of a selected temperature and humidity within the chamber and to minimize contamination of the nematodes and host organisms.

FIG. 1 shows the harvesting area 14 containing a plurality of trays 24 arranged one above another that support nematode infected host organisms. A side view of the harvesting area 14, enclosed in an incubation chamber 12, is shown in FIG. 2 and an enlarged top view of the harvesting area 14 containing tray 24 is shown in FIG. 3. FIG. 4 shows a side view of an individual tray 24.

FIGS. 1, 2 and 6 show a support frame 15 supporting the harvesting area 14, the collection system 19 and the water dispensing system 17 of the apparatus 10. Referring to FIGS. 1, 2 and 6, the base portion 46 defines the beginning of the support frame 15. A vertically extending rear support piece 48 extends from the base portion 46. A collection tray support piece. 76 extends outwardly substantially perpendicularly attached to the vertically extending rear support piece 48. The collection tray support piece 76 extends beyond the distal edge of the incubation chamber but not far enough to interfere with the collection system 19 drain tube 60. The collection tray support piece 76 provides support for the positioning the collection tray 18 at a slight angle, via support wedges 58, to funnel dispensed water in the direction of the water outlet drain tube 60.

In the embodiments shown in FIGS. 1, 2 and 6, the vertically extending rear support piece 48 provides apertures 39 for the holding tray support arms 35, which serve a dual function as water conduits in this embodiment, to perpendicularly pass therethrough to support the holding trays and to provide water to the harvesting area 14. The water inlet conduit 50 may provide water to a plurality of trays 24 by splitting the main conduit 37(*a*) into a plurality of sub conduits 37(*b*) and 37(*c*), which may pass through a plurality of rear support piece apertures 39 which are vertically equidistant from each other. The rear support piece apertures 39 are sized to accommodate a plurality of water conduits 37.

FIGS. 1, 2 and 5–7 show a plurality of trays 24 for the support, inoculation and incubation of nematode infected host organisms. FIG. 4 shows an individual tray. The tray 24 comprises a substantially flat bottom perforated piece 26 having raised side portions 28. In the embodiments shown, the tray 24 comprises a rectangular flat bottom perforated piece 26 with four sides, where two opposite sides are longer than the two adjacent sides. In FIGS. 1–4, the raised side portions 28 accommodate two apertures 32 spaced equidistant from the tray corners and spaced equidistant from the center portion of the tray 24. The apertures 32 accommodate the holding tray support arms 35 that function to suspend the trays 24. The apertures 32 are sized to accommodate insertion of horizontally extending support arms 35. In a preferred embodiment, the side portions 28 are constructed by bending the sides of the perforated bottom portion 26 upwardly until forming a 90-degree angle with the perforated bottom portion 26. This embodiment is shown in FIG. 4, wherein the tray 24 is constructed entirely of the primary perforated bottom piece by bending the sides upward and so does not require additional hardware or fasteners.

In the embodiments shown in FIGS. 1–6, the holding tray support arms 35 allow for the flow of water therethrough, functioning as a dual purpose horizontal water conveyance conduit and support arm. Thus, this embodiment features holding tray support arms that are a part of the water conveyance system 17. Water enters the apparatus 10 through the water inlet conduit 50 wherein the flow may be adjusted by a water supply control valve 52. Opening and closing of the water supply control valve may be done manually, but preferably it is controlled by a timer 22. In FIGS. 1, 5 and 6, an arrow represents the inflow of water through the water inlet conduit 50 and into the water conduits 37 and then to the water conveyance and holding tray support rods 35.

The end caps 38 prevent the flow of water out of the distal ends of the water conveyance and support rods 35 thereby forcing water to exit through numerous variably placed atomizer nozzles 34.

Water is dispensed from the water conveyance and support rods 35 through atomizer nozzles 34, wherein atomizer nozzles 34 may be variably positioned along water conveyance and support rod 35. Atomizer nozzles 34 function to dispense water in a fine mist or spray, which facilitates removal of nematodes from nematode host organisms without destruction of the nematode host organism body.

FIG. 3 shows a top view of the embodiments shown in FIGS. 1 and 2; specifically, a tray 24 in the harvesting area 14 is depicted. Atomizer nozzles 34 located at various positions along the water conveyance and support rods 35 are positioned at an angle to further defer the spray of mist from directly targeting the nematode infected host organisms. The flat bottom surface 26 of the tray 24 supports the nematode infected host organisms represented by an X.

The fourth system of the apparatus 10 is the collection system 19. Referring to FIGS. 1–3, 5 and 6, the collection tray 18 extends beyond the sides of the trays 24, or beyond the sides of the harvesting area 14. In FIGS. 1–3, 5 and 6, the collection tray 18 comprises a rectangular configuration similar to that of the holding trays 24, but constructed of a non-porous material. The collection tray 18 comprises a flat bottom portion 42 and raised side walls 40. The side walls 40 act as retaining walls to prevent the overflow of nematode enriched water and dispensed water and aid in funneling the water toward the water outlet drain 62, shown in FIG. 2.

As shown in FIGS. 1–3 and 5–7, the collection tray is preferably positioned at an angular configuration facilitating the flow of dispensed water towards the water outlet drain 62. The water outlet drain 62 connects to a drain tube 60 which is connected to an optional collection pipe 66 (not shown in FIGS. 6 and 7). Water from the water dispensing system 17 flows through the drain and into the drain tube. The optional collection pipe 66 may be used to attach additional units of the apparatus 10, concentrating dispensed water from all units into one collection pipe 66. For example, several individual apparatus 10 may be positioned side by side for the mass production of nematodes. The configuration of each apparatus will be the same, however the water outlet hose 60 will feed into a collection pipe 66. The collection pipe 66 serves as a general conduit facilitating the transport of dispensed water from all apparatus 10 to a general location.

At the end of the collection pipe, or in embodiments where a collection pipe is not used, the drain tube drains into a collection funnel 70. Referring to FIGS. 1, 5 and 6, a filter 68 is placed on top of the collection funnel 70 to filter any residual debris. Residual debris may occur from the removal of nematodes from the host organism. Although the perforated bottom piece 26 of tray 24 is specifically designed to allow passage of nematodes while retaining the nematode infected host, the perforations do not prevent passage of all debris.

A diffuser 72 converts the liquid flow from the collection pipe 66 into a fine mist or spray directed towards the filter 68. The mist from the diffuser 72 filters through the filter and passed through the collection funnel 70. Nematode-enriched water that has been filtered of debris is then passed along to a collection container as shown by the solid arrow. The collection container is not shown.

The following example is provided to describe the invention in greater detail. It is intended to illustrate, not to limit, the invention.

EXAMPLE 1

Production of Entomopathogenic Nematodes in the Greater Wax Moth, *Galleria melonella*

Approximately 500 *Galleria melonella* larvae were placed in each of several trays of the type shown and described in FIGS. 1, 2 and 3. Larvae were inoculated with infective juveniles of one of two different species, *Steinernema carpocapsae* or *Heterorhabditis bacteriphora*. Inoculation was performed either by dipping the trays into a suspension of nematodes or by hand-spraying the larvae with the nematode suspension.

Trays were stacked into the harvesting area of an apparatus as shown in FIG. 2 (harvesting area enclosed in an incubation chamber) and incubated at room temperature in 100% relative humidity for 7–8 days. Prior to harvesting, black cadavers were removed from the trays.

Automatic harvest of the nematodes was performed by contacting the nematode-infected insect cadavers with free water as follows. Mist cycles were activated for 3-minute periods at 4-hour, washing the emergent infective juveniles into the collecting tray and further into the storage and concentration area as shown in FIG. 1.

For clean-up of the system, all filters (made of organdy) were disposed of. Trays and other portions of the apparatus were washed with soap and water, and a disinfectant rinse was flushed through the water delivery system and sprayed into the harvesting area.

The present invention is not limited to the embodiments described and exemplified above, but is capable of variation and modification within the scope of the appended claims.

I claim:

1. An apparatus for the production of nematodes comprising:

a) a harvesting area comprising at least one holding tray comprising perforations, wherein the perforations are of a size to retain nematode-infected hosts while allowing passage therethrough of nematodes that emerge from the nematode-infected hosts;

b) a water dispenser for dispensing water about the harvesting area; and c) a collection system for collecting dispensed water from the harvesting area, the dispensed water containing nematodes from the nematode-infected hosts.

2. The apparatus of claim 1, which further comprises a storage vessel for storing the collected dispensed water containing the nematodes.

3. The apparatus of claim 2, which further comprises a concentrator for concentrating nematodes in the collected dispensed water.

4. The apparatus of claim 1, contained within an incubation chamber.

5. The apparatus of claim 4, wherein the incubation chamber is maintained at a pre-determined temperature and humidity.

6. The apparatus of claim 1, wherein the harvesting area comprises a plurality of trays arranged one above another.

7. The apparatus of claim 1, wherein the water dispenser includes a system of water conveyance having at least one nozzle for dispensing water.

8. The apparatus of claim 7, wherein the position of at least one nozzle is adjustably positioned so as to direct the water onto the nematode-infected hosts in the holding tray.

9. The apparatus of claim 7, comprising a plurality of holding trays and wherein the water conveyance system comprises at least one nozzle to dispense water to each of the holding trays.

10. The apparatus of claim 9, wherein the water conveyance system comprises one or more horizontally extending support arms that support the holding trays and convey the water.

11. The apparatus of claim 1, wherein the water collection system is gravitationally or pressure assisted or both.

12. The apparatus of claim 11, wherein the collection system is gravitationally assisted and comprises a collection tray that directs the dispensed water to a drain.

13. The apparatus of claim 12, further comprising a filter for removing insect host debris from the dispensed water.

14. A nematode production system comprising a plurality of the apparatus of claim 1.

15. The nematode production system of claim 14, contained within an incubation chamber.

16. A method for the production of nematodes comprising the steps of:

a) inoculating a selected host organism with infective juvenile nematodes;

b) incubating the nematode-infected hosts under conditions wherein the population of nematodes within the hosts expands;

c) harvesting the expanded population of nematodes from the nematode-infected hosts; and d) collecting the harvested nematodes;

wherein the harvesting and collecting are performed within an apparatus comprising:

i) a harvesting area comprising at least one holding tray comprising perforations, wherein the perforations are of a size to retain nematode-infected hosts while allowing passage therethrough of nematodes that emerge from the nematode-infected hosts;

ii) a water dispenser for dispensing water about the harvesting area; and iii) a collection system for collecting dispensed water from the harvesting area, the dispensed water containing nematodes from the nematode-infected hosts.

17. The method of claim 16, wherein the host organisms are inoculated by placing the organisms on the holding tray and dipping the tray into a suspension of infective juvenile nematodes.

18. The method of claim 16, wherein the host organisms are inoculated by placing the organisms on the holding tray and spraying the organisms with a suspension of infective juvenile nematodes.

19. The method of claim 16, wherein the incubating is performed in the apparatus used for harvesting and collecting the nematodes.

20. The method of claim 19, wherein the incubating is performed at a pre-determined temperature and humidity.

21. The method of claim 16, wherein the harvesting is performed by contacting the incubated, nematode-infected hosts with water dispensed through the water dispenser.

22. The method of claim 21, wherein the water dispensing is controlled by a timing device and the contacting occurs at pre-determined intervals for a pre-determined duration.

23. The method of claim 16, wherein the nematode host organism is an insect larva.

24. The method of claim 23, wherein the insect is *Galleria melonella* or *Tenebrio molitor*.

25. The method of claim 16, wherein the nematode is a species of Steinernema or Heterorhabditis.

* * * * *